US012758763B2

(12) United States Patent
Brown et al.

(10) Patent No.: US 12,758,763 B2
(45) Date of Patent: Oct. 13, 2026

(54) ESTIMATING MAXIMUM FLOW THROUGH A CIRCULATORY SUPPORT DEVICE

(71) Applicant: Abiomed, Inc., Danvers, MA (US)

(72) Inventors: Samuel Brown, Danvers, MA (US); Qing Tan, Danvers, MA (US); Mohammed Alwatban, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 432 days.

(21) Appl. No.: 18/327,957

(22) Filed: Jun. 2, 2023

(65) Prior Publication Data

US 2023/0390547 A1 Dec. 7, 2023

Related U.S. Application Data

(60) Provisional application No. 63/348,533, filed on Jun. 3, 2022.

(51) Int. Cl.
*A61M 60/546* (2021.01)

(52) U.S. Cl.
CPC ... *A61M 60/546* (2021.01); *A61M 2205/3334* (2013.01)

(58) Field of Classification Search
None
See application file for complete search history.

(56) References Cited

U.S. PATENT DOCUMENTS 11,357,968 B2 6/2022 El Katerji et al.
2012/0095280 A1* 4/2012 Timms ................ F04D 13/0633 600/16
2018/0078159 A1* 3/2018 Edelman ............ A61B 5/02141
2018/0311422 A1* 11/2018 Greatrex ............. A61M 60/824
2018/0353667 A1* 12/2018 Moyer ................. A61B 5/0215

FOREIGN PATENT DOCUMENTS

WO WO20220261580 A1 12/2022

OTHER PUBLICATIONS

International Search Report and Written Opinion mailed Sep. 9, 2023 for International Application No. PCT/US2023/024281.

* cited by examiner

*Primary Examiner* — Mallika D Fairchild
(74) *Attorney, Agent, or Firm* — Pierce Atwood LLP

(57) ABSTRACT

Methods and apparatus for estimating maximum flow for a heart pump are described. The method comprises receiving data relating motor current to differential pressure measured for a predetermined speed of a motor of the heart pump, extrapolating based on the received data, a first value for the motor current at which the differential pressure is zero, and determining a maximum flow value through the heart pump at the predetermined speed of the motor of the heart pump based, at least in part, on the first value for the motor current.

20 Claims, 14 Drawing Sheets

ESTIMATING MAXIMUM FLOW THROUGH A CIRCULATORY SUPPORT DEVICE

RELATED APPLICATIONS

This application claims the benefit under 35 U.S.C. § 119(e) of U.S. Provisional Patent Application No. 63/348,533, entitled "ESTIMATING MAXIMUM FLOW THROUGH A CIRCULATORY SUPPORT DEVICE," filed Jun. 3, 2022, the entire contents of which is incorporated herein by reference.

FIELD OF INVENTION

The disclosure relates to estimating maximum flow through a circulatory support device.

BACKGROUND

Fluid pumps, such as blood pumps, are used in the medical field in a wide range of applications and purposes. An intravascular blood pump is a pump that can be advanced through a patient's vasculature, i.e., veins and/or arteries, to a position in the patient's heart or elsewhere within the patient's circulatory system. For example, an intravascular blood pump may be inserted via a catheter and positioned to span a heart valve. The intravascular blood pump is typically disposed at the end of the catheter. Once in position, the pump may be used to assist the heart and pump blood through the circulatory system and, therefore, temporarily reduce workload on the patient's heart, such as to enable the heart to recover after a heart attack. An exemplary intravascular blood pump is available from ABIOMED, Inc., Danvers, MA under the tradename Impella® heart pump.

Such pumps can be positioned, for example, in a cardiac chamber, such as the left ventricle, to assist the heart. In this case, the blood pump may be inserted via a femoral artery by means of a hollow catheter and introduced up to and into the left ventricle of a patient's heart. From this position, the blood pump inlet draws in blood and the blood pump outlet expels the blood into the aorta. In this manner, the heart's function may be replaced or at least assisted by operation of the pump.

An intravascular blood pump is typically connected to a respective external heart pump controller that controls the heart pump, such as motor speed, and collects and displays operational data about the blood pump, such as heart signal level, battery temperature, blood flow rate and plumbing integrity. An exemplary heart pump controller is available from ABIOMED, Inc. under the trade name Automated Impella Controller™. The controller raises alarms when operational data values fall beyond predetermined values or ranges, for example if a leak, suction, and/or pump malfunction is detected. The controller may include a video display screen upon which is displayed a graphical user interface configured to display the operational data and/or alarms.

SUMMARY

Described herein are systems and methods for estimating the maximum flow through a circulatory support device. The maximum flow may be used, for example, during operation of the circulatory support device to calculate flow through the device.

In some embodiments of the present technology, a method of estimating maximum flow for a heart pump is provided.

The method comprises receiving data relating motor current to differential pressure measured for a predetermined speed of a motor of the heart pump, extrapolating based on the received data, a first value for the motor current at which the differential pressure is zero, and determining a maximum flow value through the heart pump at the predetermined speed of the motor of the heart pump based, at least in part, on the first value for the motor current.

In some embodiments, a method of estimating maximum flow for a heart pump is provided. The method comprises receiving data relating motor current to differential pressure measured for a predetermined speed of a motor of the heart pump, extrapolating based on the received data, a first value for the motor current at which the differential pressure is zero, and determining a maximum flow value through the heart pump at the predetermined speed of the motor of the heart pump based, at least in part, on the first value for the motor current.

In at least one aspect, extrapolating the first value comprises linearly extrapolating the first value based on a first portion of the data relating motor current to differential pressure. In at least one aspect, the data relating motor current to differential pressure includes a second portion, the first portion and the second portion separated by an elbow region, and extrapolating the first value based on the first portion of data comprises identifying the elbow region in the data, and identifying the first portion of the data used for extrapolation based on the identified elbow region. In at least one aspect, the elbow region includes an elbow point and a predetermined number of samples on either side of the elbow point, and identifying the first portion of the data used for extrapolation based on the identified elbow region comprises identifying the first portion of the data outside of the elbow region.

In at least one aspect, determining the maximum flow value through the heart pump at the predetermined motor speed comprises extrapolating, from a flow curve that relates flow through the pump to motor current at the predetermined motor speed, the maximum flow value through the heart pump. In at least one aspect, extrapolating the maximum flow value comprises linearly extrapolating the maximum flow value based on a first portion of the flow curve. In at least one aspect, the flow curve includes a second portion, the first portion of the flow curve and the second portion of the flow curve separated by an elbow region, and extrapolating the maximum flow value based on a first portion of the flow curve comprises identifying the elbow region in the flow curve, and identifying the first portion of the flow curve used for extrapolation based on the identified elbow region. In at least one aspect, the elbow region includes an elbow point and a predetermined number of samples on either side of the elbow point, and identifying the first portion of the flow curve used for extrapolation based on the identified elbow region comprises identifying the first portion of the flow curve outside of the elbow region.

In at least one aspect, the method further comprises generating, based at least in part, on measured data from a plurality of heart pumps, an average flow curve, and the flow curve that relates flow through the pump to motor current at the predetermined motor speed is the average flow curve. In at least one aspect, the measured data from a plurality of heart pumps comprises a plurality of flow curves, each of which relates flow through the pump to motor current at the predetermined motor speed one of the plurality of pumps, and generating the average flow curve comprises aligning a maximum measured flow of each of the plurality of curves, and generating the average flow curve based on the aligned plurality of flow curves.

In at least one aspect, the method further comprises configuring the heart pump to estimate flow through the heart pump during operation based, at least in part, on the maximum flow value. In at least one aspect, configuring the heart pump to estimate flow through the heart pump during operation comprises associating in at least one memory of the heart pump, the maximum flow value and the predetermined motor current speed.

In at least one aspect, the method further comprises generating, based at least in part, on measured data from a plurality of heart pumps, an average curve relating motor current to differential pressure at the predetermined speed of the motor, and the data relating motor current to differential pressure comprises the average curve relating motor current to differential pressure. In at least one aspect, the measured data from a plurality of heart pumps comprises a plurality of curves, each of which relates motor current to differential pressure for one of the plurality of pumps, and generating the average curve relating motor current to differential pressure comprises aligning a maximum motor current of each of the plurality of curves, and generating the average curve based on the aligned plurality of curves.

In some embodiments, a heart pump is provided. The heart pump comprises a rotor, a motor configured to drive rotation of the rotor at one or more speeds, and at least one controller configured to control the motor to operate at a first speed of the one or more speeds, measure the motor current of the motor while adjusting a differential pressure across the heart pump to generate data relating motor current to differential pressure for the first speed of the motor, extrapolate based on the measured data, a first value for the motor current at which the differential pressure is zero, determine a maximum flow value through the heart pump at the first speed of the motor based, at least in part, on the first value for the motor current, and configure the heart pump to measure flow through the heart pump based, at least in part, on the determined maximum flow value.

In at least one aspect, extrapolating the first value comprises linearly extrapolating the first value based on a first portion of the data relating motor current to differential pressure. In at least one aspect, the data relating motor current to differential pressure includes a second portion, the first portion and the second portion separated by an elbow region, and extrapolating the first value based on the first portion of data comprises identifying the elbow region in the data, and identifying the first portion of the data used for extrapolation based on the identified elbow region. In at least one aspect, the elbow region includes an elbow point and a predetermined number of samples on either side of the elbow point, and identifying the first portion of the data used for extrapolation based on the identified elbow region comprises identifying the first portion of the data outside of the elbow region.

In at least one aspect, determining the maximum flow value through the heart pump at the predetermined motor speed comprises extrapolating, from a flow curve that relates flow through the pump to motor current at the predetermined motor speed, the maximum flow value through the heart pump. In at least one aspect, extrapolating the maximum flow value comprises linearly extrapolating the maximum flow value based on a first portion of the flow curve. In at one aspect, the flow curve includes a second portion, the first portion of the flow curve and the second portion of the flow curve separated by an elbow region, and extrapolating the maximum flow value based on a first portion of the flow curve comprises identifying the elbow region in the flow curve, and identifying the first portion of the flow curve used for extrapolation based on the identified elbow region. In at least one aspect, the elbow region includes an elbow point and a predetermined number of samples on either side of the elbow point, and identifying the first portion of the flow curve used for extrapolation based on the identified elbow region comprises identifying the first portion of the flow curve outside of the elbow region.

In at least one aspect, the at least one controller is further configured to generate, based at least in part, on measured data from a plurality of heart pumps, an average flow curve, and wherein the flow curve that relates flow through the pump to motor current at the predetermined motor speed is the average flow curve. In at least one aspect, the measured data from a plurality of heart pumps comprises a plurality of flow curves, each of which relates flow through the pump to motor current at the predetermined motor speed one of the plurality of pumps, and wherein generating the average flow curve comprises aligning a maximum measured flow of each of the plurality of curves, and generating the average flow curve based on the aligned plurality of flow curves.

In at least one aspect, configuring the heart pump to estimate flow through the heart pump during operation comprises associating in at least one memory of the heart pump, the maximum flow value and the predetermined motor current speed. In at least one aspect, the at least one controller is further configured to generate, based at least in part, on measured data from a plurality of heart pumps, an average curve relating motor current to differential pressure at the predetermined speed of the motor, and wherein the data relating motor current to differential pressure comprises the average curve relating motor current to differential pressure. In at least one aspect, the measured data from a plurality of heart pumps comprises a plurality of curves, each of which relates motor current to differential pressure for one of the plurality of pumps, and wherein generating the average curve relating motor current to differential pressure comprises aligning a maximum motor current of each of the plurality of curves, and generating the average curve based on the aligned plurality of curves.

In some embodiments, a controller for a heart pump is provided. The controller comprises at least one hardware processor. The at least one hardware processor is configured to receive data relating motor current to differential pressure measured for a predetermined speed of a motor of the heart pump, extrapolate based on the received data, a first value for the motor current at which the differential pressure is zero, determine a maximum flow value through the heart pump at the predetermined speed of the motor of the heart pump based, at least in part, on the first value for the motor current, and configure the controller to determine flow through the heart pump based, at least in part, on the determined maximum flow value.

In at least one aspect, extrapolating the first value comprises linearly extrapolating the first value based on a first portion of the data relating motor current to differential pressure. In at least one aspect, the data relating motor current to differential pressure includes a second portion, the first portion and the second portion separated by an elbow region, and extrapolating the first value based on the first portion of data comprises identifying the elbow region in the data, and identifying the first portion of the data used for extrapolation based on the identified elbow region. In at least one aspect, the elbow region includes an elbow point and a predetermined number of samples on either side of the elbow point, and identifying the first portion of the data used for extrapolation based on the identified elbow region comprises identifying the first portion of the data outside of the elbow region.

In at least one aspect, determining the maximum flow value through the heart pump at the predetermined motor speed comprises: extrapolating, from a flow curve that relates flow through the pump to motor current at the predetermined motor speed, the maximum flow value through the heart pump. In at least one aspect, extrapolating the maximum flow value comprises linearly extrapolating the maximum flow value based on a first portion of the flow curve. In at least one aspect, the flow curve includes a second portion, the first portion of the flow curve and the second portion of the flow curve separated by an elbow region, and extrapolating the maximum flow value based on a first portion of the flow curve comprises identifying the elbow region in the flow curve, and identifying the first portion of the flow curve used for extrapolation based on the identified elbow region. In at least one aspect, the elbow region includes an elbow point and a predetermined number of samples on either side of the elbow point, and identifying the first portion of the flow curve used for extrapolation based on the identified elbow region comprises identifying the first portion of the flow curve outside of the elbow region.

In at least one aspect, the at least one hardware processor is further configured to generate, based at least in part, on measured data from a plurality of heart pumps, an average flow curve, and wherein the flow curve that relates flow through the pump to motor current at the predetermined motor speed is the average flow curve. In at least one aspect, the measured data from a plurality of heart pumps comprises a plurality of flow curves, each of which relates flow through the pump to motor current at the predetermined motor speed one of the plurality of pumps, and wherein generating the average flow curve comprises aligning a maximum measured flow of each of the plurality of curves, and generating the average flow curve based on the aligned plurality of flow curves.

In at least one aspect, configuring the heart pump to estimate flow through the pump during operation comprises associating in at least one memory of the heart pump, the maximum flow value and the predetermined motor current speed. In at least one aspect, the at least one hardware processor is further configured to generate, based at least in part, on measured data from a plurality of heart pumps, an average curve relating motor current to differential pressure at the predetermined speed of the motor, and wherein the data relating motor current to differential pressure comprises the average curve relating motor current to differential pressure. In at least one aspect, the measured data from a plurality of heart pumps comprises a plurality of curves, each of which relates motor current to differential pressure for one of the plurality of pumps, and wherein generating the average curve relating motor current to differential pressure comprises aligning a maximum motor current of each of the plurality of curves, and generating the average curve based on the aligned plurality of curves.

DETAILED DESCRIPTION

Traditionally, blood flow through a circulatory support device, such as a catheter-based heart pump inserted into a ventricle of the patient, is calculated based on motor speed and motor current sensed from the pump motor. For instance, data characterizing the relationship between flow and motor current (also referred to herein as "Q vs. MC curves" or "flow curves") for each of a plurality of motor speeds may be stored, and the stored data and a measured motor current value may be used to estimate the flow when the pump motor is operated at a particular speed. For each of the flow curves, the point representing maximum flow when the pump is operating at a particular speed corresponds to the point during which the differential pressure (i.e., the pressure between the ventricle and aorta) is zero. The inventors have recognized that determining the maximum flow point of a flow curve is, in practice, challenging to determine with precision. As described in more detail below, some embodiments of the present technology relate to techniques for determining the maximum flow value for a flow curve.

Figure 1A:
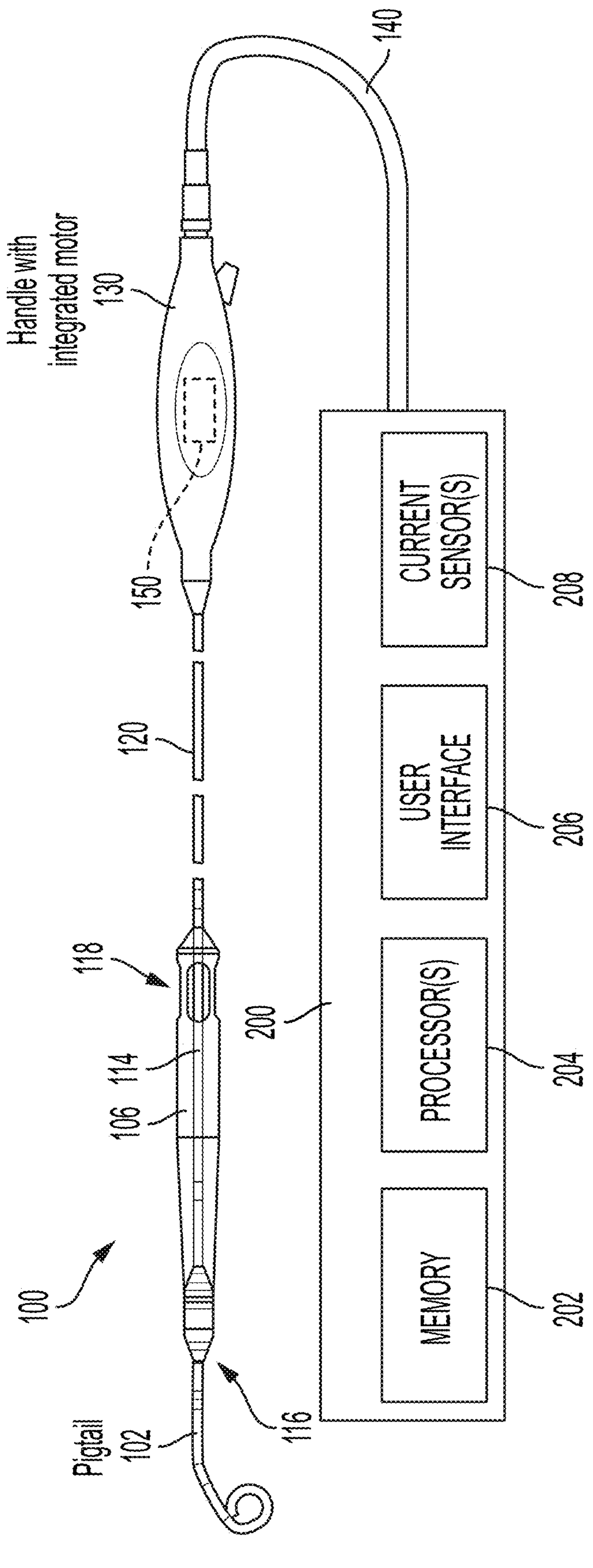
FIG. 1A illustrates a pump system in accordance with some embodiments of the present technology.
Figure 1B:
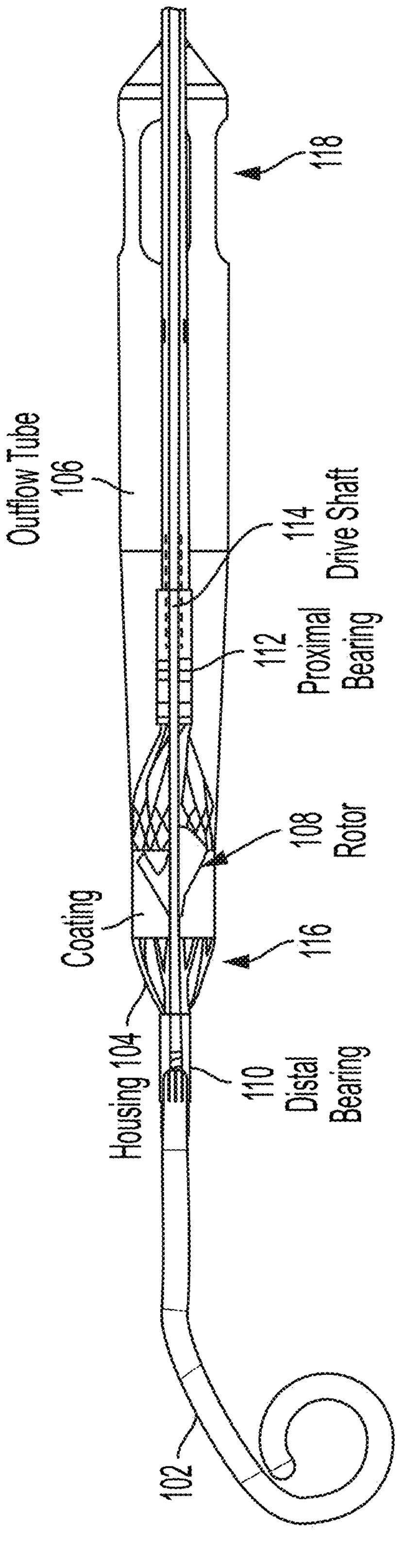
FIG. 1B is a cross-sectional view of a portion of the pump system of FIG. 1A.

A pump system 100 for use with some embodiments of the present technology is shown in FIGS. 1A and 1B. As shown, pump system 100 is coupled to a control unit 200. Pump 100 includes a distal atraumatic tip 102, a pump housing 104 surrounding a rotor 108, an outflow tube 106, distal bearing 110, proximal bearing 112, inlet 116, outlet 118, catheter 120, handle 130, cable 140, and motor 150. Pump housing 104 may be configured as a frame structure formed by a mesh with openings which may, at least in part, be covered by an elastic material. A proximal portion of pump housing 104 extends into and is mounted in the hollow interior of outflow tube 106, and a distal portion of pump housing 104 extends distally beyond the distal end of outflow tube 106. The exposed openings in the pump housing 104 extending distally beyond outflow tube 106 form the inlet 116 of pump 100. The proximal end of outflow tube 106 includes a plurality of openings that form the outlet 118 of pump 100. Rotor 108 is rotationally mounted between distal bearing 110 and proximal bearing 112, and is coupled to a distal end of drive shaft 114. Drive shaft 114 is flexible and extends through catheter 120, through the hollow interior of outflow tube 106, into handle 130 and is coupled to motor 150, which is housed in handle 130. The proximal end of handle 130 is coupled via cable 140 to control unit 200. A fluid may be circulated through the catheter 120 proximate to the drive shaft 114 and in the space surrounding the distal bearing 110 and proximal bearing 112 to lubricate those components and reduce friction during operation of the pump 100.

Control unit 200 includes one or more memory 202, one or more processors 204, user interface 206, and one or more current sensors 208. Processor(s) 204 may comprise one or more microcontrollers, one or more microprocessors, one or more application specific integrated circuits (ASICs), one or more digital signal processors, program memory, or other computing components. Processor(s) 204 is communicatively coupled to the other components (e.g., memory 202, user interface 206, current sensor(s) 208) of control unit 200 and is configured to control one or more operations of pump 100. As a non-limiting example, control unit 200 may be implemented as an Automated Impella Controller™ from ABIOMED, Inc., Danvers, MA. In some aspects, memory 202 is included as a portion of processor(s) 204 rather than being provided as a separate component.

During operation, processor(s) 204 is configured to control the electrical power delivered to motor 150 (e.g., by controlling a power supply (not shown)) by a power supply line (not shown) in cable 140, thereby controlling the speed of the motor 150. Current sensor(s) 208 may be configured to sense motor current associated with an operating state of the motor 150, and processor(s) 204 may be configured to receive the output of current sensor(s) 208 as a motor current signal. Processor(s) 204 may further be configured to determine a flow through the pump 100 based, at least in part, on the motor current signal and the motor speed, as described in more detail below. Current sensor(s) 208 may be included in control unit 200 or may be located along any portion of the power supply line in cable 140. Additionally or alternatively, current sensor(s) 208 may be included in motor 150 and processor(s) 204 may be configured to receive the motor current signal via a data line (not shown) in cable 140 coupled to processor(s) 204 and motor 150.

Memory 202 may be configured to store computer-readable instructions and other information for various functions of the components of control unit 200. In one aspect, memory 202 includes volatile and/or non-volatile memory, such as, an electrically erasable programmable read-only memory (EEPROM).

User interface 206 may be configured to receive user input via one or more buttons, switches, knobs, etc. Additionally, user interface 206 may include a display configured to display information and one or more indicators, such as light indicators, audio indicators, etc., for conveying information and/or providing alerts regarding the operation of pump 100.

Pump 100 is designed to be insertable into a patient's body, e.g., into a left ventricle of the heart, with an introducer system. In one aspect, housing 104, rotor 108, and outflow tube 106 are radially compressible to enable pump 100 to achieve a relatively small outer diameter of, for example, 9 Fr (3 mm) during insertion. When pump 100 is inserted into the patient, e.g., into a left ventricle, handle 130 and motor 150 remain disposed outside the patient. During operation, motor 150 is controlled by processor(s) 204 to drive rotation of drive shaft 114 and rotor 108 to convey blood from inlet 116 to outlet 118. It is to be appreciated that rotor 108 may be rotated by motor 150 in reverse to convey blood in the opposite direction (in this case, the openings of 118 form the inlet and the openings of 116 form the outlet). In one aspect, pump 100 is intended to be used during high-risk procedures for a duration of up to six hours, though it should be understood that the technology described herein is not limited to any particular types of procedures and/or use durations.

Figures 2A, 2B, 2C:
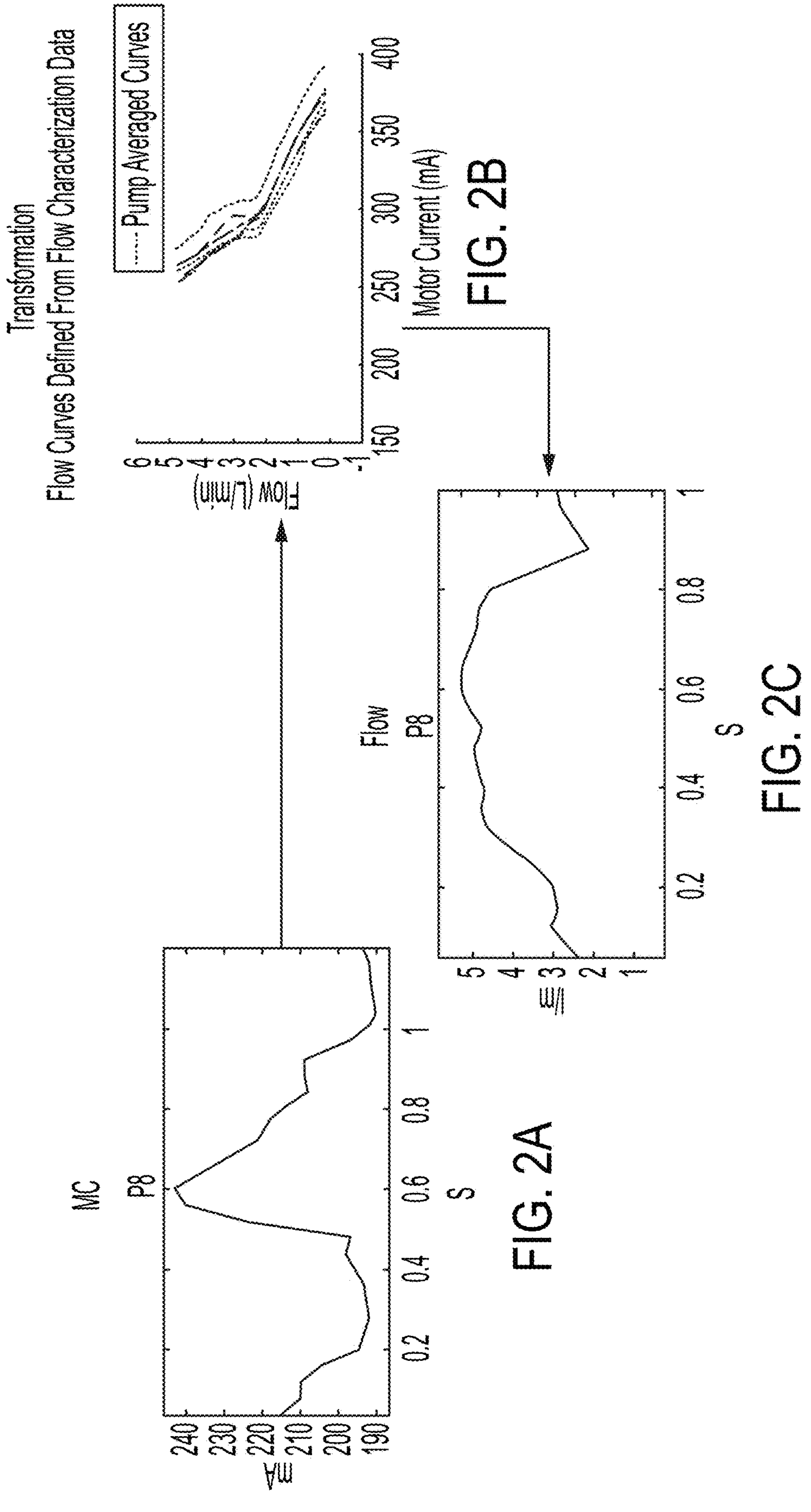
FIGS. 2A-2C schematically illustrate a process for determining flow through a heart pump based on a measured motor current signal during operation of the heart pump.

FIGS. 2A-2C schematically illustrate a technique for calculating flow based on a motor current signal within a time window in accordance with some embodiments. FIG. 2A illustrates a motor current (MC) signal during a single cardiac cycle with motor current in milliamps (mA) being represented on the y-axis and time being represented on the x-axis. Based on the value of the motor current signal, the corresponding flow through the pump may then be calculated using a stored relationship (also referred to herein as "flow curves" or "Q vs. MC curves") that relates flow values through the pump and motor current, an example of which is illustrated in FIG. 2B, with flow being represented on the y-axis and motor current being represented on the x-axis. For instance, values represented graphically as a flow curve may be stored in memory as a lookup table that is used to associate motor current values with flow values at a particular motor speed.

The flow curves at different motor speeds may be determined during an "offline" testing procedure that approximates normal operation of the device in a patient. During the testing procedure, flow and motor current are measured at different motor speeds, and a plurality of flow curves, one for each motor speed, are determined based on the measured data. FIG. 2B shows multiple flow curves determined for a plurality of pumps tested at the same motor speed. An average flow curve across the plurality of tested pumps may be stored and used to calculate flow during operation of the pump. Flow calculation based on sensed motor current may be implemented in control unit 200 of pump system 100.

FIG. 2C shows an example of a flow signal generated based on a motor current signal (e.g., the motor current signal of FIG. 2A) received, for example from one or more motor current sensors 208, as described above in connection with FIG. 1A. A time window of predetermined length (e.g., between 1 and 4 seconds) of the motor current signal may be analyzed, and a motor current value associated with maximum flow through the pump may be determined. Flow though the pump is based on the pressure difference between the inlet and outlet of the pump through which blood is conveyed when the pump is in operation. During systole, the pressure difference between the inlet and outlet of the pump is zero, resulting in the maximum flow through the pump. Depending on the pump design, the minimum motor current value during the time window may correspond to the maximum flow (at systole) or the maximum motor current value during the time window may correspond to the maximum flow (at systole). To account for instabilities in the motor current signal over time, the measured motor current signal may be adjusted based, at least in part, on an offset value between the measured motor current value corresponding to maximum flow (e.g., the minimum motor current value) and the motor current value corresponding to maximum flow as indicated in the stored flow curve at the particular speed at which the motor current is operating. The flow through the pump may then be determined, at least in part, on the adjusted motor current signal.

Figure 2D:
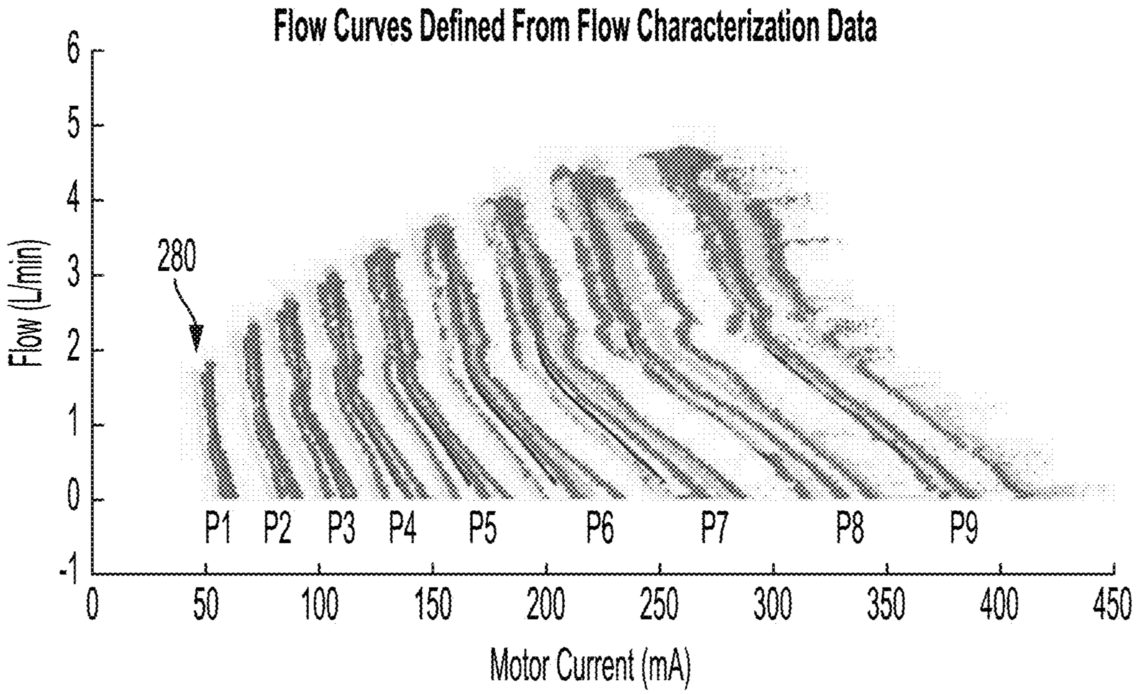
FIG. 2D illustrates a plurality of flow curves that relate flow through a heart pump and motor current that may be used to determine flow through the heart pump during operation.

FIG. 2D shows a plurality of flow curves at different motor speeds, labeled in FIG. 2D as P1 through P9, with P1 being the slowest speed and P9 being the fastest speed of the motor. Similar to the plot in FIG. 2B which illustrated measurements at a single motor speed, in the plot of FIG. 2D, multiple flow curves are also shown at each of the motor speeds P1-P9. For each of the motor speeds, values corresponding to a single flow curve (e.g., as an average of the flow curves shown) may be stored as a lookup table that may be used to calculate flow during operation of a pump, as described above. The point on one of the flow curves (for the motor speed P1) corresponding to maximum flow is labeled as 280.

The inventors have recognized and appreciated that accurately determining the point on a flow curve corresponding to maximum flow is important for, among other things, accurate determination of the offset value used to adjust the motor current signal during operation of the heart pump. However, measurement of the maximum flow point during the "offline" testing procedure used to create the flow curves is challenging, in part, because it is difficult to implement the scenario in which the pressure across the inlet and outlet of the heart pump is zero (e.g., stimulating the system when the heart would be in systole). To this end, some embodiments are directed to techniques for estimating the maximum flow point for a flow curve based on incomplete data measured during an offline testing procedure. A more precise measurement of the maximum flow value may improve the flow determination calculations when the heart pump is in operation.

Figure 3:
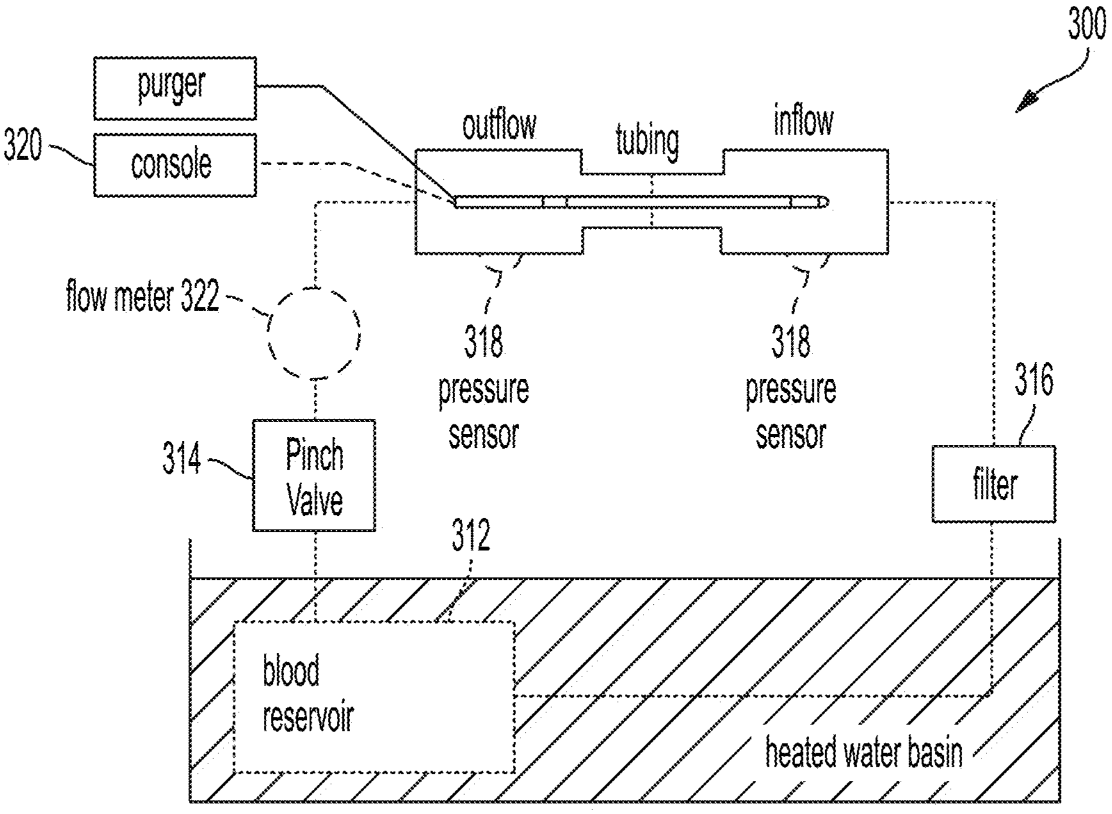
FIG. 3 illustrates a system that may be used to measure data characterizing flow through a heart pump in accordance with some embodiments.

FIG. 3 schematically illustrates a flow characterization system 300 that may be used during an offline testing procedure to obtain flow (Q), motor current (MC) and differential pressure (dP) data from which various curves relating these quantities may be determined. As shown, a pump is arranged in a flow loop that includes a blood reservoir 312 disposed in a heated water basin to keep the circulating blood at a desired temperature, a pinch valve 314, and a filter 316 configured to filter the blood prior to being returned to the blood reservoir 312. For each of a plurality of motor speeds (e.g., P1-P9 described above), the differential pressure (dP) as measured by the pressure sensors 318 is gradually changed by console 320 to simulate the pumping cycle of the heart. The generated flow (as measured by flow meter 322), the drawn motor current (MC) and the experienced differential pressure (dP) are measured as dP is adjusted. In some embodiments, dP is adjusted by applying different amounts of back pressure onto the pump.

As described above, when in operation, the maximum flow through the pump occurs when the differential pressure is equal to zero (i.e., during systole). In the ideal case then, it would be desirable to simulate systole using system 300 by providing a back pressure as close to zero as possible. However, in practice, system 300 struggles to keep up when presented with low back pressures. Additionally, the pump itself produces its own pressure difference, so an additional pump would need to be inserted into the loop to counter this intrinsic pressure difference of the pump, resulting in a complicated setup. In some embodiments, rather than attempting to simulate systole conditions precisely, system 300 is controlled to provide the smallest possible back pressure that the system can handle, which results in an incomplete data set that does not data for when dP=0. As discussed in further detail below, the maximum flow at the dP=0 point is estimated using the techniques described herein from the incomplete data.

Figure 4:
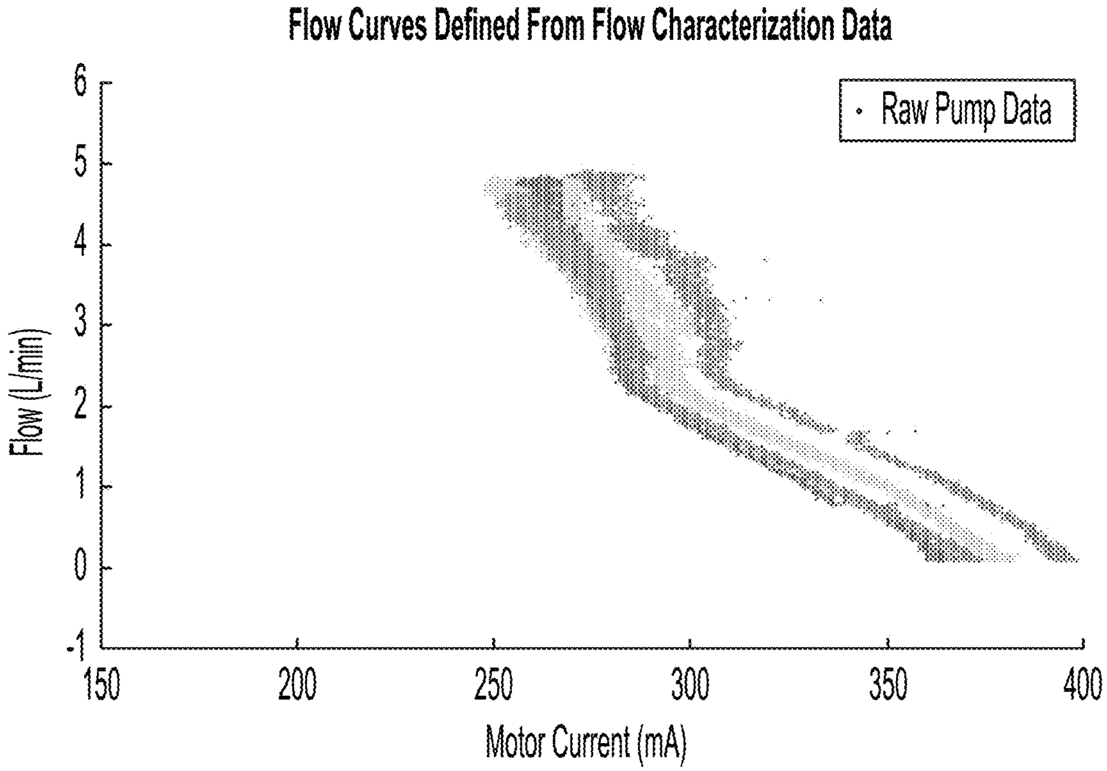
FIG. 4 illustrates raw flow data measured from a plurality of pumps using the flow characterization system of FIG. 3.
Figure 5:
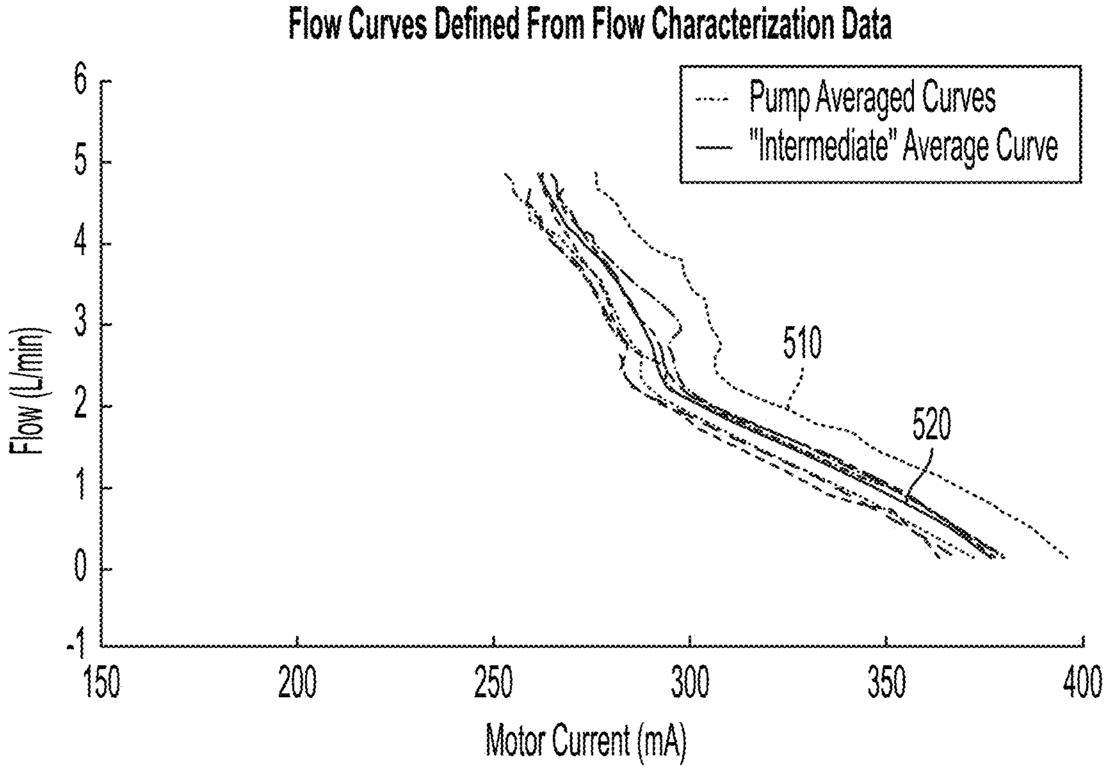
FIG. 5 graphically illustrates a process for determining an average flow curve based on a plurality of individual pump average flow curves in accordance with some embodiments.

In some embodiments, for each motor speed (e.g., P-level) a point cloud of data relating flow and motor current may be generated by, for example, adjusting the differential pressure across the pump in system 300 (e.g., by applying different back pressures onto the pump). FIG. 4 illustrates an example of such point cloud data collected for each of a plurality of different pumps inserted into flow loop of system 300. For each of the pumps, an average flow curve was created as shown in FIG. 5. As an example, average flow curve 510 is shown for a pump corresponding to raw pump data on the far right of the plot in FIG. 4. In some embodiments, the average curve is generated by finding the maximum and minimum flow generated at a particular motor speed. A plurality of bins (e.g., 50 bins) may be created across the range of flows from minimum to maximum, and the average curves may be created by calculating the average motor current in each of the plurality of bins. It should be appreciated, however, that other techniques may alternatively be used to transform the point cloud for a pump to an average flow curve for the pump.

After creating an average flow curve for each tested pump (e.g., average flow curve 510), an average flow curve across all tested pumps for a particular motor speed (e.g., P-level) may be determined. The average flow curve across all tested pumps is shown in FIG. 5 as flow curve 520. As shown, flow curves may be characterized by having a first (e.g., upper) portion at higher flow rates and a second (e.g., lower) portion at lower flow rates, with an elbow region between the first and second portions. In the example shown in FIG. 5, the first portion has a steeper slope compared to the second portion. In some embodiments, the average flow curve across pumps is generated separately for the first portion and the second portion.

Figure 6:
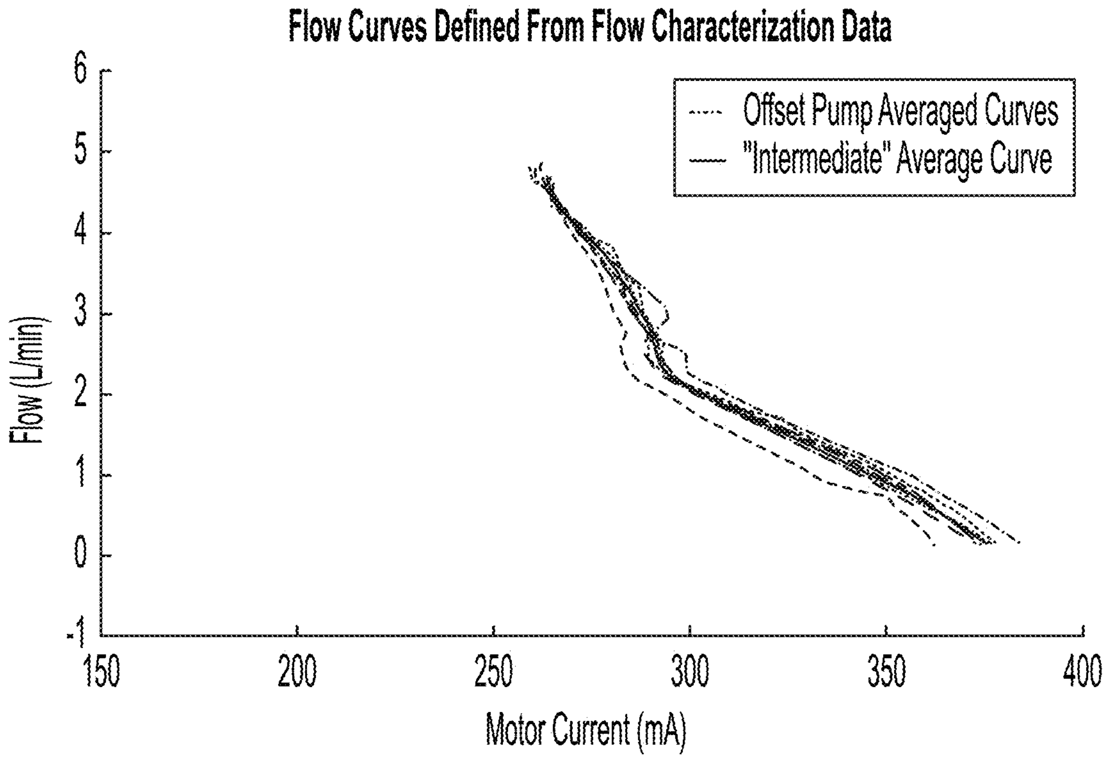
FIG. 6 graphically illustrates a process for aligning flow curves for individual pumps prior to generating an average flow curve across pumps in accordance with some embodiments.
Figure 7:
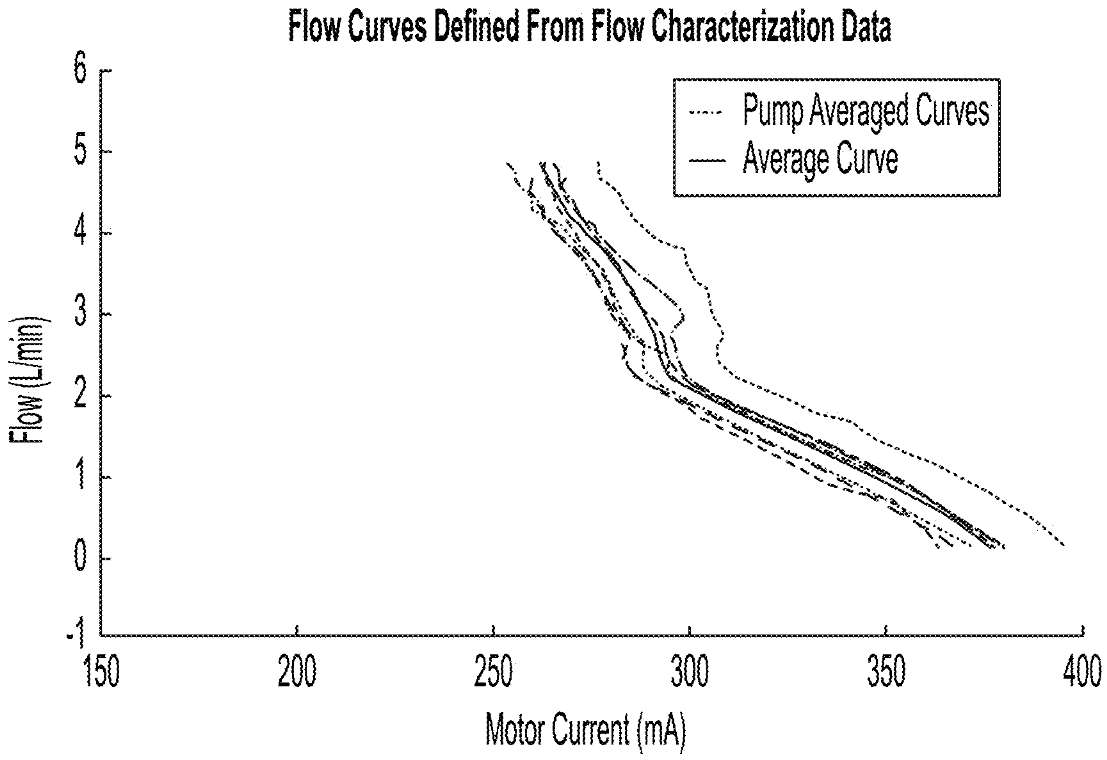
FIG. 7 graphically illustrates a process for generating an average flow curve across pumps following the alignment process shown in FIG. 6 in accordance with some embodiments.
Figure 8:
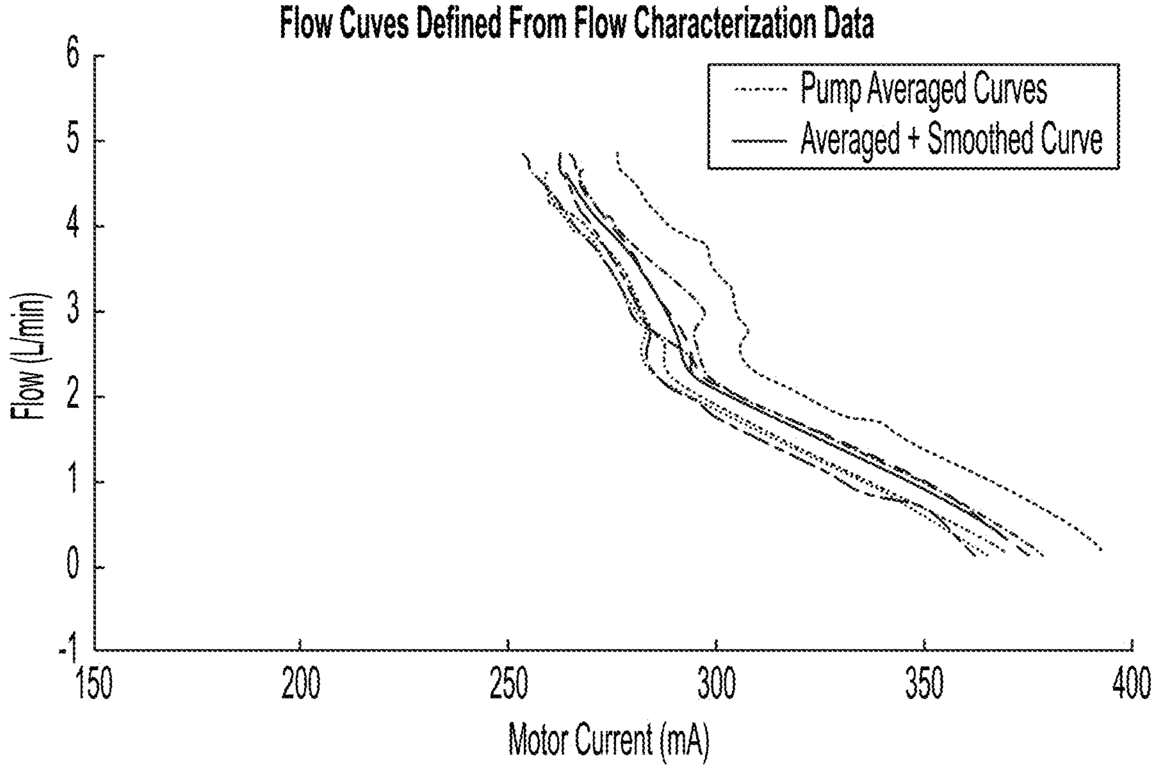
FIG. 8 graphically illustrates a process for generating an average flow curve across pumps that has been smoothed in accordance with some embodiments.

When generating flow data characterization sets (e.g., the raw flow data in FIG. 4), the highest flow generated by different tested pumps may vary due, for example, to hardware differences with the pumps. If this difference was not taken into account when averaging across tested pumps, only some of the tested pumps would have data contributing to the across pump average at the higher flow rates. However, if one or more of the pumps generating the higher flows was an outlier (e.g., the corresponding flow curves were far to the right or left in FIG. 5), the high flow region in the average flow curve across pumps would not be straight (or approximately straight), but would instead appear crooked compared to the rest of the curve, which may impact the extrapolation process for the high-flow part of the curve as described in more detail below. In some embodiments, to account for pump-to-pump differences at the high flow part of the flow curves, the individual average flow curves may be aligned (e.g., offset horizontally) as shown in FIG. 6, and an "intermediate" average flow curve (solid line in FIG. 6) may be determined based on the aligned average flow curves. All individual pump average flow curves may then be aligned on the intermediate average flow curve's highest flow point as shown in FIG. 7, and an average flow curve across pumps can be generated. In some embodiments, the average flow curve across pumps is then smoothed using a filter (e.g., a small Gaussian kernel) as shown in FIG. 8, resulting in an average flow curve for the motor current speed (e.g., P-level). The process shown in FIGS. 4-7 can then be repeated for the raw flow data collected for each of the P-levels, resulting in one average flow curve per P-level.

Figure 9:
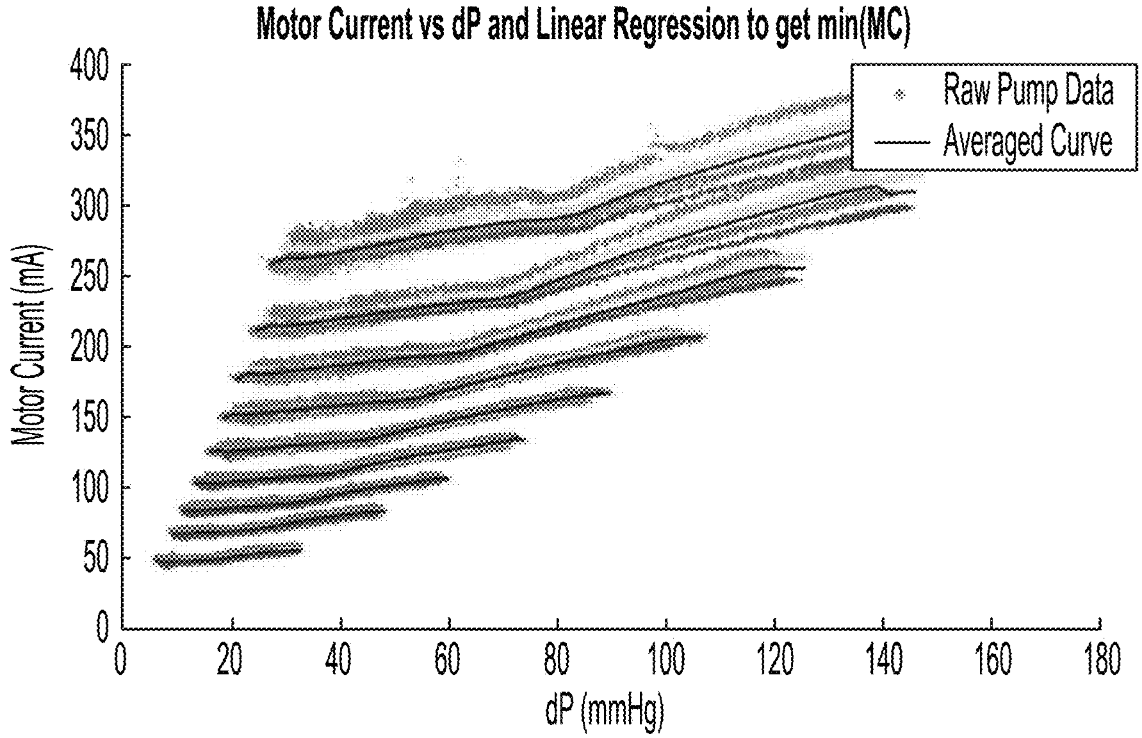
FIG. 9 graphically illustrates a process for generating average motor current (MC) vs. differential pressure (dP) curves for each of a plurality of motor speeds of a heart pump in accordance with some embodiments.

A similar process as that shown in FIGS. 4-7 may be used to generate average motor current (MC) vs. differential pressure (dP) curves for each P-level, as shown in FIG. 9. For instance, a plurality of bins (e.g., 50 bins) may be created between the minimum measured motor current value and the maximum measured motor current value at each motor speed, and the average MC value within each of the plurality of bins may be used to generate the average MC vs. dP curve for the motor speed. The average MC vs. dP curves can then be used to determine a motor current that corresponds to a value of dP=0, as described in more detail below.

Figure 10A:
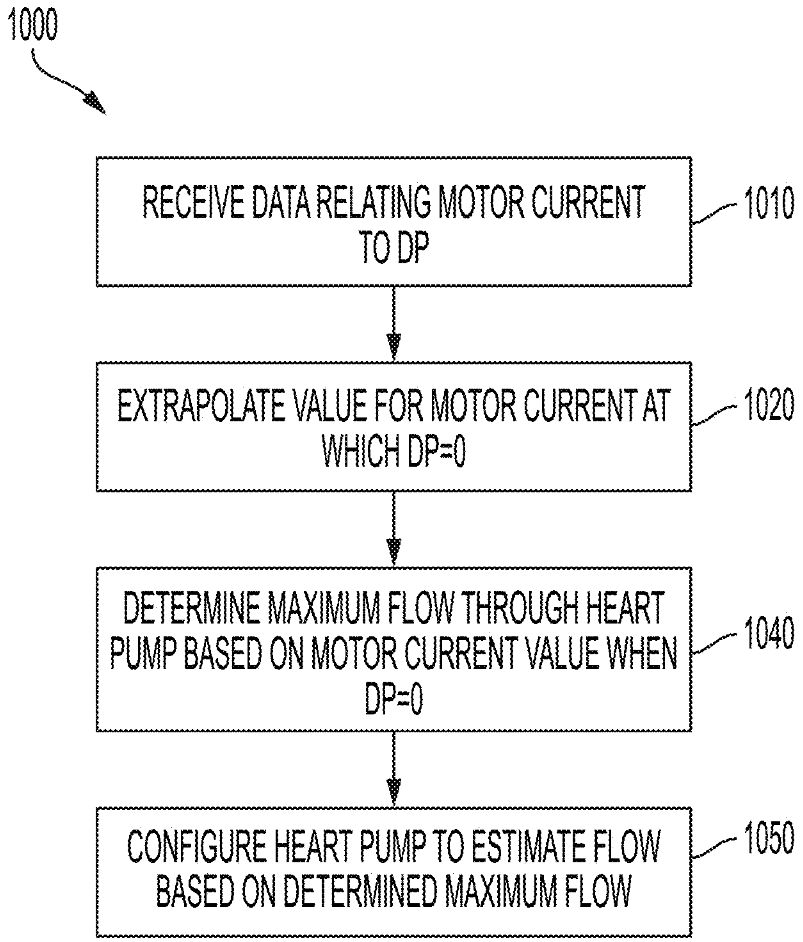
FIG. 10A illustrates a process for determining a maximum flow through a heart pump in accordance with some embodiments.

FIG. 10A shows a flowchart of a process 1000 for determining a maximum flow through a heart pump in accordance with some embodiments. In act 1010, data relating motor current to differential pressure is received. For instance the data may correspond to the average MC vs. dP curves illustrated in FIG. 9, determined using an offline testing procedure (e.g., using system 300 shown in FIG. 3) and one or more of the processing techniques (e.g., as shown in FIGS. 4-8) described herein.

As shown in FIG. 9, the value of the motor current corresponding to the dP=0 point is not known based on measured data. Process 1000 proceeds to act 1020, where the motor current value (e.g., the minimum motor current value) corresponding to a differential pressure value of dP=0 is determined for each of the plurality of motor current speeds. In some embodiments, the motor current value at dP=0 is determined by extrapolating based on a portion of the data received in act 1010. The MC vs. dP curve for each P-level may be approximated by a parametrically-linear curve including a first portion, a second portion, and an elbow region arranged between the first and second portions. The first and second portions may have different slopes, which can be distinguished using, for example derivatives (e.g., first and/or second derivative) of the curves.

In some embodiments, the elbow region of the MC vs. dP curve is identified by examining where along the curve the derivative changes more than a threshold amount to determine an elbow point, then identifying the elbow region as a region around the elbow point. For instance, the elbow point may be determined as the point with the maximum second derivative in a particular portion of the curve (e.g., the leftmost portion of the curve in FIG. 9). The elbow region may be determined as a region along the curve that includes a predetermined number of samples (e.g., 2, samples, 3, samples, 5 samples, etc.) on either side of the elbow point. The predetermined number of samples used to define the elbow region may be the same or different across P-levels. The portion of the MC vs. dP curve having lower motor current values outside of the elbow region may be considered as the first portion of the curve and the portion of the MC vs. dP curve having higher motor current values outside of the elbow region may be considered as the second portion of the curve.

Figure 11:
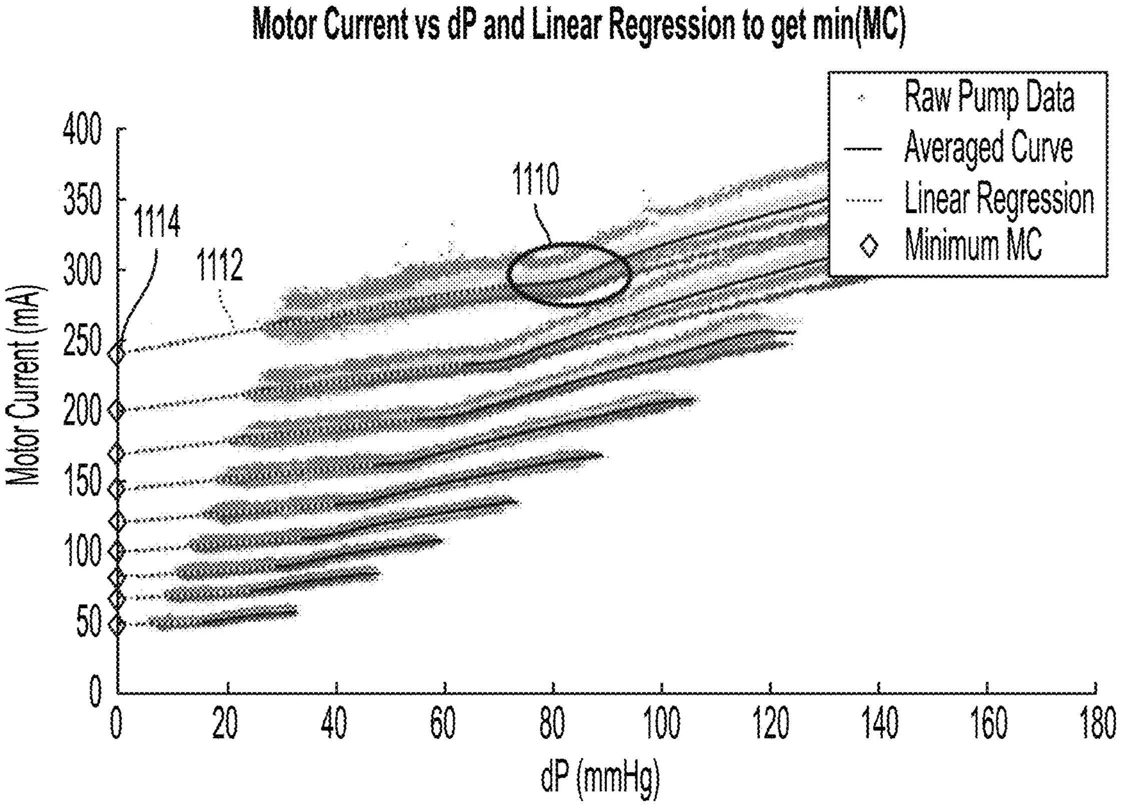
FIG. 11 graphically illustrates a process for determining a motor current value at which dP=0 in accordance with some embodiments.

To determine the motor current when dP=0, extrapolation from the first portion of the curve may be used. For instance, some embodiments use linear extrapolation from the first portion of the MC vs. dP curve to determine the value of the motor current when dP=0. FIG. 11 schematically shows this process, where, for the fastest motor speed (e.g., P9), the elbow region 1110 has been identified, and a line 1112 has been fitted to the first portion of the curve having lower motor current values outside of elbow region 1110. The point at which line 1112 intersects the y-axis (corresponding to dP=0) is determined to be the value of the minimum motor current for that motor speed. A similar procedure can be followed to determine the minimum motor currents for each of the other motor speeds, as shown. Although linear extrapolation is described as being used in some embodiments, it should be appreciated that a non-linear curve may be fit to the first portion of the curve in some embodiments to determine the minimum motor current value. Additionally, it should be appreciated that the process for determining the motor current value when dP=0 is graphically shown in FIG. 11 merely to facilitate explanation, and such graphical illustrations are not necessarily generated for all embodiments. Rather, the process for determining the motor current value when dP=0 may be performed numerically based on measured data using regression (e.g., linear regression) based on a portion of the average curve measured across pumps.

Returning to process 1000 shown in FIG. 10A, after determining the value of the motor current at which dP=0 for a particular motor speed, process 1000 proceeds to act 1040, where the maximum flow through the heart pump is determined based on the determined motor current value when dP=0. Process 1000 then proceeds to act 1050, where a heart pump (which may be a different heart pump than one of the heart pumps involved in the offline testing), is configured based on the determined maximum flow to estimate flow through the pump during operation. For instance, the maximum flow value determined in act 1040 may be associated in at least one memory of the heart pump (e.g., as a look up table) with the motor speed at which the maximum flow value was determined, and the stored data may be used to estimate flow during operation of the pump.

Figure 10B:
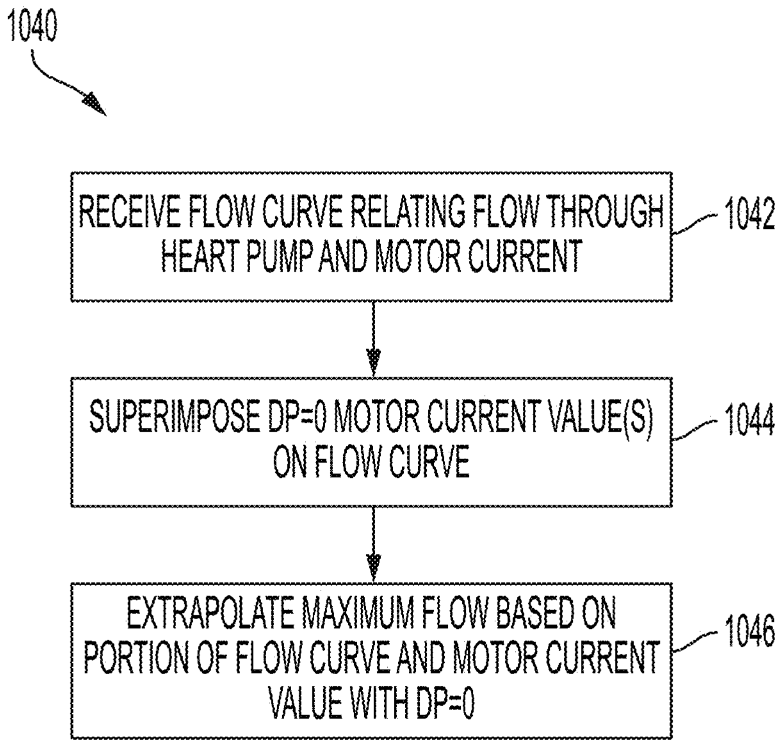
FIG. 10B illustrates a process for determining a maximum flow through a heart pump based on a determined motor current value at which dP=0 in accordance with some embodiments.
Figure 12:
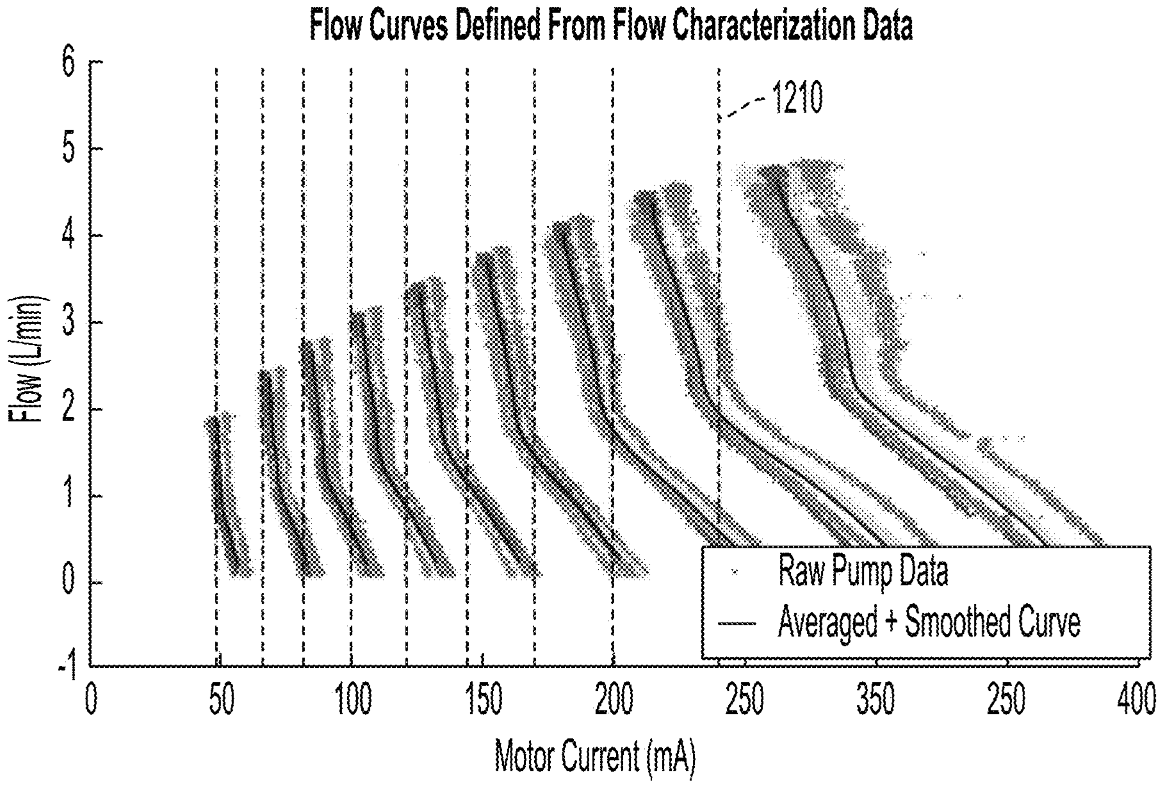
FIG. 12 graphically illustrates a process for superimposing the motor current values determined in the process of FIG. 11 on a plot of average flow curves in accordance with some embodiment.

FIG. 10B illustrates an example of how the maximum flow through a heart pump may be determined in act 1040 in accordance with some embodiments. In act 1042, a flow curve relating flow through the heart pump and motor current may be received. An example, of such a flow curve is shown and described with reference to FIG. 8, in which an average flow curve for a motor current speed is illustrated. The determination of the average flow curve may be repeated across all motor speeds resulting in a plot as shown in FIG. 12. In act 1044, the motor current value determined for dP=0 (e.g., in act 1030 of FIG. 10A) may be superimposed on the flow curve, an example, of which is shown in FIG. 12 as the vertical dashed line 1210 for the highest motor speed P9. As shown in FIG. 12, motor current values for dP=0 determined at other motor speeds may also be superimposed on a plurality of flow curves determined for a plurality of motor speeds.

Figure 13:
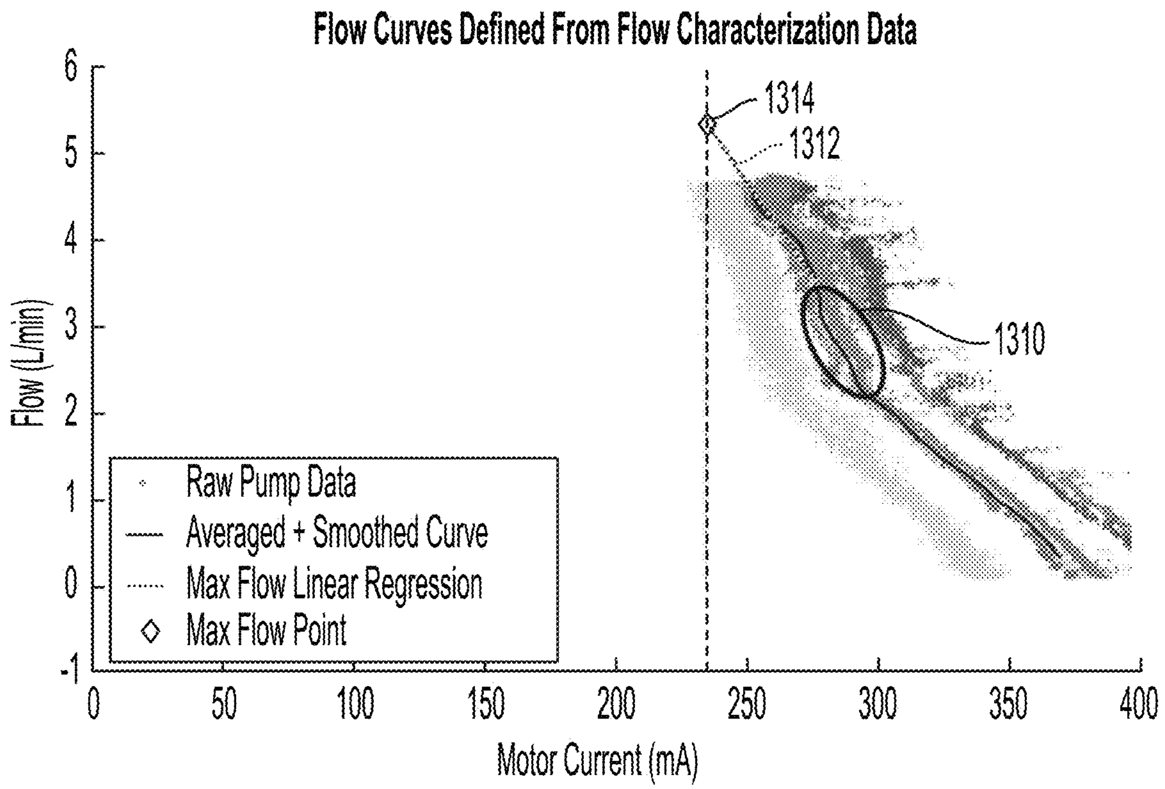
FIG. 13 graphically illustrates a process for determining a maximum flow value through a heart pump based on an average flow curve at a predetermined motor speed and the determined motor current value at which dP=0 in accordance with some embodiments.
Figure 14:
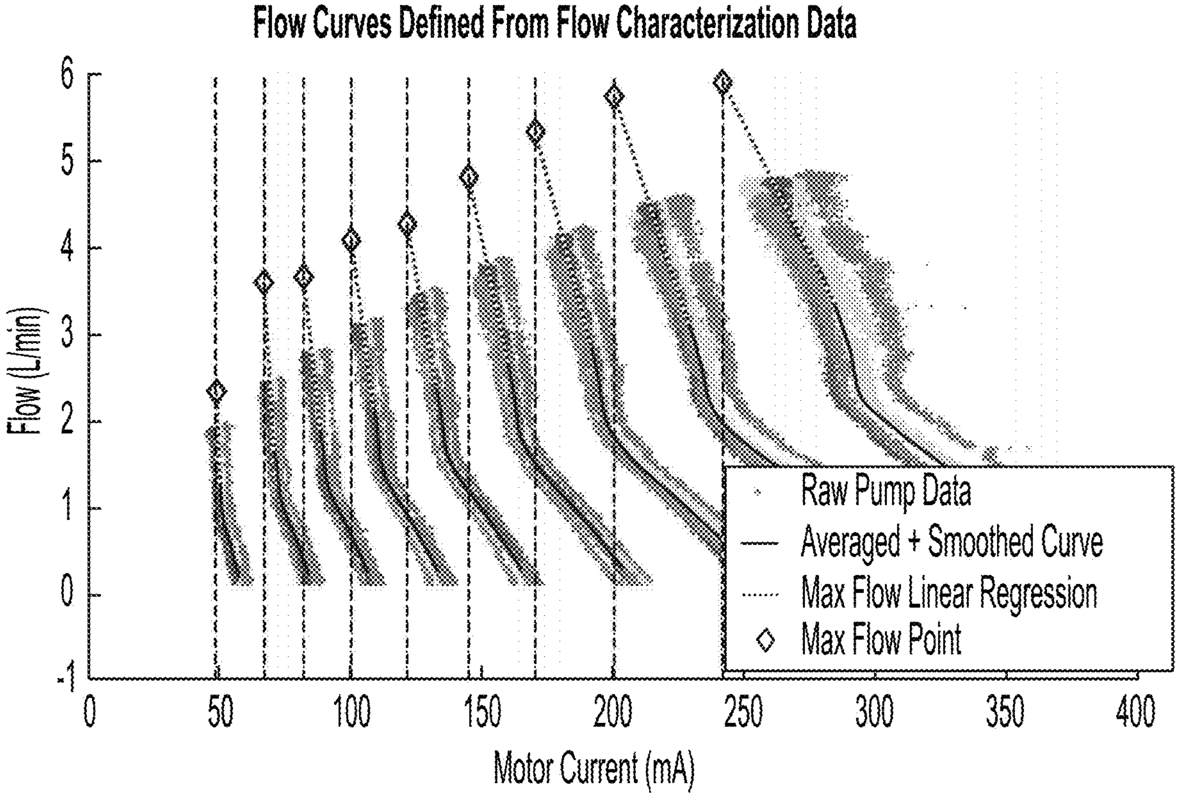
FIG. 14 graphically illustrates a process for determining the maximum flow value through a heart pump at each of a plurality of predetermined motor speeds of the heart pump.

In act 1046, the value of maximum flow through the pump is determined by extrapolating based on a portion of the flow curve and the motor current value when dP=0 for a particular motor speed. In some embodiments, the process for extrapolation may be similar to (though not necessarily identical as) that described above in connection with FIG. 11. For instance, as shown schematically in FIG. 13, an elbow region 1310 may be identified, and the extrapolation may be performed based on a first (e.g., upper) region of the flow curve to identify the maximum flow value. In some embodiments, linear extrapolation is used to fit a line 1312 to the first portion of the flow curve, and the point 1314 at which the line 1312 intersects the superimposed motor current value corresponding to dP=0 is determined to be the maximum flow value for that particular motor speed. A similar procedure may be performed for each of the motor speeds (e.g., P1-P9) to determine a corresponding maximum flow value for each motor speed, as shown schematically in FIG. 14. As described briefly above, the determined maximum flow values and corresponding motor speeds may be used to configure a heart pump to more accurately determine flow, when used in operation. Additionally, it should be appreciated that the process for determining the maximum flow through the pump is graphically shown merely to facilitate explanation, and such graphical illustrations are not necessarily generated for all embodiments. Rather, the process for determining the maximum flow may be performed numerically based on measured data using regression (e.g., linear regression) based on a portion of the average curve measured across pumps.

Having thus described several aspects and embodiments of the technology set forth in the disclosure, it is to be appreciated that various alterations, modifications, and improvements will readily occur to those skilled in the art. For example, process 1000 includes two discrete acts 1030 and 1040 to determine the maximum flow through the pump at a particular motor speed by performing extrapolation twice. In some embodiments, the processing in acts 1030 and 1040 may be combined into a single step in which extrapolation is performed only once, but in three dimensions (Q, MC, dP) based on the flow characterization data measured during the offline testing procedure and any additional processing used to generate average curves as described herein. In yet other embodiments, human labeled data may be used to train a machine learning algorithm to determine the maximum flow values for each motor speed. In yet further embodiments, the unique behaviors observed in the [Q, MC, dP] data sets measured during the offline testing procedure may be parameterized using one or more models, and the maximum flow value and/or minimum motor current value may be estimated based, at least in part, on the determined parameters.

In some further modifications, while aspects of the present technology relate to an apparatus and methods for detection, separation, purification, and/or quantification of bacteria as described herein, the inventors have recognized that such apparatus and methods are broadly applicable to other organisms of interest, e.g. viruses, yeast, and aspects of the technology are not limited in this respect.

Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of estimating flow through a heart pump, the method comprising:

receiving data relating motor current to differential pressure measured for a predetermined speed of a motor of the heart pump;

extrapolating based on the received data, a first value for the motor current at which the differential pressure is zero;

determining a maximum flow value through the heart pump at the predetermined speed of the motor of the heart pump based, at least in part, on the first value for the motor current;

configuring the heart pump to estimate flow through the heart pump during operation when implanted in a patient by associating in at least one memory of the heart pump, the maximum flow value and the predetermined speed of the motor of the heart pump;

receiving, during operation of the heart pump at the predetermined speed, a motor current signal indicating an amount of current provided to a motor of the heart pump over time;

adjusting the motor current signal based on the maximum flow value to produce an adjusted motor current signal;

determining the flow through the heart pump based, at least in part, on the adjusted motor current signal; and outputting an indication of the flow on a user interface associated with the heart pump.

2. The method of claim 1, wherein extrapolating the first value comprises linearly extrapolating the first value based on a first portion of the data relating motor current to differential pressure.

3. The method of claim 2, wherein:

the data relating motor current to differential pressure includes a second portion, the first portion and the second portion separated by an elbow region, and extrapolating the first value based on the first portion of data comprises:

identifying the elbow region in the data; and identifying the first portion of the data used for extrapolation based on the identified elbow region.

4. The method of claim 3, wherein the elbow region includes an elbow point and a predetermined number of samples on either side of the elbow point, and identifying the first portion of the data used for extrapolation based on the identified elbow region comprises identifying the first portion of the data outside of the elbow region.

5. The method of claim 1, wherein determining the maximum flow value through the heart pump at the predetermined speed of the motor of the heart pump comprises:

extrapolating, from a flow curve that relates flow through the heart pump to motor current at the predetermined speed of the motor of the heart pump, the maximum flow value through the heart pump.

6. The method of claim 5, wherein extrapolating the maximum flow value comprises linearly extrapolating the maximum flow value based on a first portion of the flow curve.

7. The method of claim 6, wherein:

the flow curve includes a second portion, the first portion of the flow curve and the second portion of the flow curve separated by an elbow region, and extrapolating the maximum flow value based on a first portion of the flow curve comprises:

identifying the elbow region in the flow curve; and identifying the first portion of the flow curve used for extrapolation based on the identified elbow region.

8. The method of claim 7, wherein the elbow region includes an elbow point and a predetermined number of samples on either side of the elbow point, and identifying the first portion of the flow curve used for extrapolation based on the identified elbow region comprises identifying the first portion of the flow curve outside of the elbow region.

9. The method of claim 5, further comprising:

generating, based at least in part, on measured data from a plurality of heart pumps, an average flow curve, and wherein the flow curve that relates flow through the heart pump to motor current at the predetermined speed of the motor of the heart pump is the average flow curve.

10. The method of claim 9, wherein the measured data from a plurality of heart pumps comprises a plurality of flow curves, each of which relates flow through the heart pump to motor current at the predetermined speed of the motor for one of the plurality of heart pumps, and wherein generating the average flow curve comprises:

aligning a maximum measured flow of each of the plurality of curves; and generating the average flow curve based on the aligned plurality of flow curves.

11. The method of claim 1, further comprising:

generating, based at least in part, on measured data from a plurality of heart pumps, an average curve relating motor current to differential pressure at the predetermined speed of the motor, and wherein the data relating motor current to differential pressure comprises the average curve relating motor current to differential pressure.

12. The method of claim 11, wherein the measured data from a plurality of heart pumps comprises a plurality of curves, each of which relates motor current to differential pressure for one of the plurality of heart pumps, and wherein generating the average curve relating motor current to differential pressure comprises:

aligning a maximum motor current of each of the plurality of curves; and generating the average curve based on the aligned plurality of curves.

13. A heart pump, comprising:

a rotor;

a motor configured to drive rotation of the rotor at one or more speeds; and at least one controller configured to:

control the motor to operate at a first speed of the one or more speeds;

measure a motor current of the motor while adjusting a differential pressure across the heart pump to generate data relating motor current to differential pressure for the first speed of the motor;

extrapolate based on the data, a first value for the motor current at which the differential pressure is zero;

determine a maximum flow value through the heart pump at the first speed of the motor based, at least in part, on the first value for the motor current;

configure the heart pump to measure flow through the heart pump at the first speed based, at least in part, on the determined maximum flow value, wherein configuring the heart pump to measure flow through the heart pump comprises associating in at least one memory of the heart pump, the maximum flow value and the first speed;

receive, during operation of the heart pump at the first speed, a motor current signal indicating an amount of current provided to a motor of the heart pump over time;

adjust the motor current signal based on the maximum flow value to produce an adjusted motor current signal;

determine the flow through the heart pump based, at least in part, on the adjusted motor current signal; and output an indication of the flow on a user interface associated with the heart pump.

14. The heart pump of claim 13, wherein extrapolating the first value comprises linearly extrapolating the first value based on a first portion of the data relating motor current to differential pressure, the data relating motor current to differential pressure includes a second portion, the first portion and the second portion separated by an elbow region, and extrapolating the first value based on the first portion of data comprises:

identifying the elbow region in the data; and identifying the first portion of the data used for extrapolation based on the identified elbow region.

15. The heart pump of claim 13, wherein determining the maximum flow value through the heart pump at the first speed comprises:

extrapolating, from a flow curve that relates flow through the heart pump to motor current at the first speed, the maximum flow value through the heart pump.

16. A controller for a heart pump, the controller comprising:

at least one hardware processor configured to:

receive data relating motor current to differential pressure measured for a predetermined speed of a motor of the heart pump;

extrapolate based on the received data, a first value for the motor current at which the differential pressure is zero;

determine a maximum flow value through the heart pump at the predetermined speed of the motor of the heart pump based, at least in part, on the first value for the motor current;

configure the controller to determine flow through the heart pump based, at least in part, on the determined maximum flow value, wherein configuring the heart pump to measure flow through the heart pump comprises associating in at least one memory of the heart pump, the maximum flow value and the predetermined speed of the motor of the heart pump;

receive, during operation of the heart pump at the predetermined speed, a motor current signal indicating an amount of current provided to a motor of the heart pump over time;

adjust the motor current signal based on the maximum flow value to produce an adjusted motor current signal;

determine the flow through the heart pump based, at least in part, on the adjusted motor current signal; and output an indication of the flow on a user interface associated with the heart pump.

17. The controller of claim 16, wherein extrapolating the first value comprises linearly extrapolating the first value based on a first portion of the data relating motor current to differential pressure, the data relating motor current to differential pressure includes a second portion, the first portion and the second portion separated by an elbow region, and extrapolating the first value based on the first portion of data comprises:

identifying the elbow region in the data; and identifying the first portion of the data used for extrapolation based on the identified elbow region.

18. The controller of claim 16, wherein determining the maximum flow value through the heart pump at the predetermined speed of the motor of the heart pump comprises:

extrapolating, from a flow curve that relates flow through the heart pump to motor current at the predetermined speed of the motor of the heart pump, the maximum flow value through the heart pump.

19. The method of claim 1, further comprising:

determining, within a time window of the motor current signal, a first value corresponding to maximum flow through the heart pump; and determining an offset value based on the first value and the maximum flow value, wherein adjusting the motor current signal based on the maximum flow value to produce an adjusted motor current signal comprises:

adjusting the motor current signal based on the offset value.

20. The method of claim 19, wherein determining, within a time window of the motor current signal, a first value corresponding to maximum flow through the heart pump comprises determining a minimum value of the motor current signal or a maximum value of the motor current signal within the time window.

* * * * *